United States Patent [19]

Topol

[11] 3,977,830
[45] Aug. 31, 1976

[54] SILVER NITRITE REACTANT FOR MEASURING $SO_2$

[75] Inventor: Leo E. Topol, Canoga Park, Calif.

[73] Assignee: Rockwell International Corporation, El Segundo, Calif.

[22] Filed: Mar. 21, 1975

[21] Appl. No.: 560,894

[52] U.S. Cl. ............................ 23/232 R; 23/232 E; 23/254 R; 23/255 E; 204/195 S; 250/361 C; 356/181; 423/400
[51] Int. Cl.² ................ G01N 31/00; G01N 31/22; G01N 27/00; G01N 27/26
[58] Field of Search .......... 23/232 R, 232 E, 254 R, 23/254 E, 255 R, 255 E; 423/400, 402; 204/195 R, 195 S, 1 N, 1 S; 324/65 R; 356/181; 250/361 C

[56] References Cited
UNITED STATES PATENTS

| | | |
|---|---|---|
| 3,578,406 | 5/1971 | Cho et al. ........................ 23/232 R |
| 3,647,392 | 3/1972 | McGinnis ......................... 23/232 E |
| 3,677,708 | 7/1972 | Harman et al. ................... 23/232 R |

OTHER PUBLICATIONS

Mellor, J. W., "A Comprehensive Treatise on Inorganic and Theoretical Chemistry," vol. VIII, p. 483, (1947).

*Primary Examiner*—Norman Yudkoff
*Assistant Examiner*—Barry I. Hollander
*Attorney, Agent, or Firm*—L. Lee Humphries; Henry Kolin; Clark E. DeLarvin

[57] ABSTRACT

Sulphur dioxide is reacted with silver nitrite at room temperature to release nitrogen dioxide in a known ratio and the nitrogen dioxide may, then, be measured as an indication of the presence and amount of sulphur dioxide.

11 Claims, 2 Drawing Figures

SILVER NITRITE REACTANT FOR MEASURING SO₂

BACKGROUND OF THE INVENTION

1. Field of the Invention

This invention relates to methods and apparatus for measuring air pollutants and is particularly directed to methods and apparatus for measuring sulphur dioxide.

2. Description of the Prior Art

In recent years, man has realized the fact that such essential natural resources as air and water are not unlimited in abundance and that survival requires that we take steps to prevent further pollution of these resources and, where possible, capture pollutants which have previously been released.

Among the major pollutants of air are oxides of nitrogen and sulphur. Numerous methods and apparatus have been proposed heretofore for measuring the various pollutants individually. However, none of the prior art devices have been capable of measuring oxides of both nitrogen and sulphur. Separate equipment has been required to accomplish this which, obviously, greatly increases the cost of pollution detection systems. Moreover, the most popular devices for measuring sulphur dioxide have required either bubbling the polluted air through an aqueous solution or reacting the sulphur dioxide with a hydrogen flame. Unfortunately, the bubbling method requires a liquid container, which is subject to spillage, while the hydrogen flame method requires a source of hydrogen, which becomes expensive and involves some inherent danger of explosion. Moreover, the flame is subject to being blown out or otherwise extinguished, which renders the device unreliable or useless. Other prior art detectors have made only gross measurements or have required frequent recalibration.

BRIEF SUMMARY AND OBJECTS OF THE INVENTION

The disadvantages of the prior art are overcome with the present invention and a method of detecting sulphur dioxide is proposed which is simple, reliable, economical and is accurate to fractional parts per million. Moreover, the present invention functions at ambient temperatures and employs solid state components.

Furthermore, the device of the present invention is adaptable to permit measurement of sulphur dioxide by detectors which were originally intended to detect only oxides of nitrogen.

The advantages of the present invention are preferably attained by providing a quantity of silver nitrite in a solid, yet porous form, passing air which may contain sulphur dioxide through the silver nitrite to allow the sulphur dioxide to react with the silver nitrite, and detecting nitrogen dioxide displaced by said reaction as an indication of the presence and quantity of sulphur dioxide.

Accordingly, it is an object of the present invention to provide improved methods and simplified apparatus for measuring sulphur dioxide.

Another object of the present invention is to provide a method and apparatus for measuring sulphur dioxide which is simple, reliable, economical and is accurate to fractional parts per million.

A further object of the present invention is to provide a method and apparatus for measuring sulphur dioxide which is functional at ambient temperatures.

An additional object of the present invention is to provide a method and apparatus for adapting sensors of nitrogen oxides to sense sulphur dioxide also.

A specific object of the present invention is to provide a method and apparatus for measuring sulphur dioxide comprising forming a quantity of silver nitrite into a solid yet porous form, passing air which may contain sulphur dioxide through said silver nitrite to allow the sulphur dioxide to react with the silver nitrite, and detecting nitrogen dioxide displaced by said reaction as an indication of the presence and amount of said sulphur dioxide.

These and other objects and features of the present invention will be apparent from the following detailed description, taken with reference to the accompanying drawing.

DETAILED DESCRIPTION OF THE INVENTION

Figure 1:
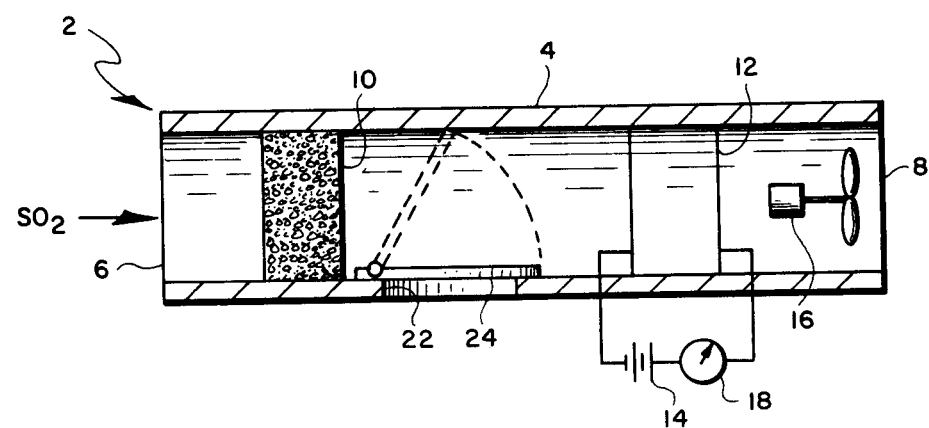
FIG. 1 is a diagrammatic representation of a device embodying the present invention, with parts shown in section.

In that form of the present invention chosen for purpose of illustration in FIG. 1, a sulphur dioxide measuring device, indicated generally at 2, is shown comprising a cylindrical housing 4 which is open at each end 6 and 8. Within the housing 4 is mounted a quantity of silver nitrite formed into a gas-permeable capsule 10. The capsule 10 may be formed by any suitable means, such as compressing the silver nitrite into a solid, yet porous, wafer or providing a pair of circular mesh discs which are secured together and are capable of retaining silver nitrite granules therebetween, yet permit passage of gas therethrough. Spaced axially along the housing 4 from the capsule 10 is a solid state detector 12 for measuring oxides of nitrogen. The detector 12 is preferably of the type shown and described in U.S. Pat. No. 3,764,269. Suitable means, such as battery 14, is provided to energize the detector 12 and, if desired, means, such as fan 16 may be provided to draw air through the device 2.

In use, air is caused to flow through the housing 4, by means of fan 16 or the like. In passing through the housing 4, the air will be forced to pass through capsule 10 and detector 12. If there is any sulphur dioxide ($SO_2$) present in the air, the sulphur dioxide will react with the silver nitrite ($AgNO_2$) yielding $4.4 \pm .01$ parts of $NO_2$ for each part of $SO_2$.

The nitrogen dioxide ($NO_2$), released by this reaction is then detected and measured by the solid state detector 12 and the amount of the nitrogen dioxide is shown by meter 18. As indicated above, the $AgNO_2$ releases about four $NO_2$ molecules for each $SO_2$ molecule it receives. Thus, since detector 12 measures the quantity of $NO_2$ present, the output of detector 12 will be equal to approximately four times the quantity of $SO_2$ present. If desired, meter 18 may be calibrated to compensate for this and to indicate the quantity of $SO_2$ directly. It has been found that this technique can accurately detect and measure the presence of $SO_2$ to fractional parts per million in air. Moreover, this technique can be carried out at ambient temperatures and is unaffected by relative humidity in the range of 30–80%. Where NO or $NO_2$ are also present in the air, it would be possible to employ the foregoing technique by placing a second solid state detector 12 in parallel with the device 2 to measure the amount of NO or $NO_2$. The output of the second detector 12 could then be subtracted from the output of the device 2, electrically, to determine the amount of $SO_2$. Alternatively, if desired, an opening 22 may be formed in the housing 4 between the capsule 10 and the detector 12 and suitable means, such as valve 24 may be provided, actuated by a solenoid or the like, to alternately close the opening 22, as seen in solid lines, or to open the opening 22 and to block passage of air through the capsule 10, as indicated by the dotted line position of valve 24. In this way, when valve 24 is in its solid line position, air will pass through capsule 10 to the detector 12 to enable the detector to measure sulphur dioxide. Alternatively, when the valve 24 is in its dotted line position, it will prevent passage of air through capsule 10 and will allow air to flow through opening 22 to detector 12 to enable the detector 12 to measure nitrogen dioxide.

Figure 2:
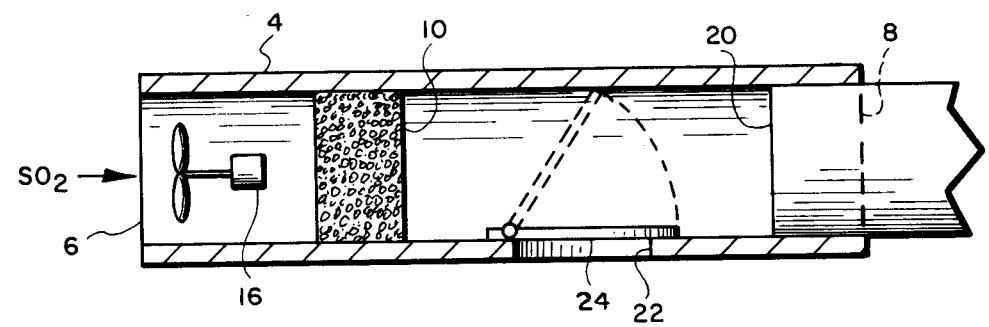
FIG. 2 is a diagrammatic representation of an alternative form of the present invention.

As shown in FIG. 2, the technique of the present invention may be employed to adapt conventional NO or $NO_2$ detectors to sense $SO_2$. This has not been possible with prior art oxide of nitrogen detectors. However, it can be accomplished quickly, easily and inexpensively with the apparatus of the present invention. As shown in FIG. 2, the adapter is similar to the device of FIG. 1, having an open ended cylindrical housing 4 in which is mounted a gas-permeable capsule 10 of silver nitrite. One end 8 of the housing 4 is formed for attachment, as by a friction fit, to the sensor 20 of a conventional NO or $NO_2$ detector. Moreover, if desired, suitable means, such as fan 16, may be mounted within the housing 4 to force air passage through the housing 4. If desired, the adapter of FIG. 2 may also be provided with a bypass opening 22 and valve 24 for the purposes set forth above relative to FIG. 1.

If the sensor 20 is part of a detector employing electrochemical, colorimetric or conductimetric methods for measuring $NO_2$, the $NO_2$ from the adapter of FIG. 2 may be measured, without preconditioning, as an indication of the amount of $SO_2$ present. If the sensor 20 is part of a chemiluminescent detector, the $NO_2$ must be reduced and measured as NO to indicate the amount of $SO_2$ passing through the adapter.

Obviously, numerous variations and modifications may be made without departing from the present invention. Accordingly, it should be clearly understood that the forms of the present invention described above and shown in the accompanying drawing are illustrative only and are not intended to limit the scope of the present invention.

I claim:

1. A sulphur dioxide measuring device comprising:
    a housing defining a gas passageway,
    a quantity of silver nitrite disposed in a gas-permeable form located in said gas passageway,
    nitrogen dioxide measuring means located downstream of said quantity of silver nitrite and in flow communication with said gas passageway, and
    means for passing a gas through said quantity of silver nitrite to allow any sulphur dioxide present in said gas to react with said silver nitrite to form nitrogen dioxide for passage to said nitrogen dioxide measuring means and thereby provide an indication of the concentration of sulphur dioxide contained in said gas.

2. The device of claim 1 wherein:
    said quantity of silver nitrite is a self-supporting, yet porous, capsule.

3. The device of claim 2 wherein:
    said capsule is formed of compacted silver nitrite.

4. The device of claim 1 wherein said nitrogen dioxide measuring means is an electrochemical detector.

5. The device of claim 1 wherein said nitrogen dioxide measuring means is a colorimetric detector.

6. The device of claim 1 wherein said nitrogen dioxide measuring means is a conductimetric detector.

7. The device of claim 1 wherein said nitrogen dioxide measuring means is a chemiluminescent detector.

8. An apparatus for adapting a detector of nitrogen dioxide to measure sulphur dioxide, said apparatus comprising:
    a housing defining a gas passageway,
    a quantity of silver nitrite disposed in a gas-permeable form located in said gas passageway,
    means for passing a gas through said quantity of silver nitrite to allow any sulphur dioxide present in said gas to react with the silver nitrite to form nitrogen dioxide, and
    means for delivering the nitrogen dioxide resulting from said reaction to said detector.

9. A method of measuring the amount of sulphur dioxide contained in a gas, said method comprising the steps of:
    passing said gas through a quantity of silver nitrite to allow any sulphur dioxide contained in said gas to react with said silver nitrite to form nitrogen dioxide, and
    measuring the nitrogen dioxide resulting from said reaction as an indication of the presence and amount of sulphur dioxide in said gas.

10. The method of claim 9 wherein:
    the reaction of sulphur dioxide with said silver nitrite is carried out at ambient temperatures.

11. The method of claim 9 wherein:
    the reaction of sulphur dioxide with said silver nitrite is carried out at a relative humidity in the range of about 30–80 percent.

* * * * *